United States Patent [19]

Wood et al.

[11] Patent Number: 5,303,600
[45] Date of Patent: Apr. 19, 1994

[54] FLUID SAMPLING RESERVOIR AND METHOD

[75] Inventors: Richard F. Wood, Miami; John I. Banu, Plantation, both of Fla.

[73] Assignee: General Oceanics, Inc., Miami, Fla.

[21] Appl. No.: 532,444

[22] Filed: Jun. 4, 1990

[51] Int. Cl.$^5$ ............................................. G01L 1/04
[52] U.S. Cl. .................................. 73/864.62; 73/864.67
[58] Field of Search .................. 73/863.31, 863.01, 864.63-864.67, 73/864.62

[56] References Cited

U.S. PATENT DOCUMENTS

| | | | |
|---|---|---|---|
| 3,242,740 | 3/1966 | Niskin | 73/863.31 |
| 3,489,012 | 1/1970 | Niskin | 73/863.31 |
| 4,302,974 | 12/1981 | Niskin | 73/864.62 |
| 4,852,413 | 8/1989 | Niskin, deceased et al. | 73/864.67 |

Primary Examiner—Robert Raevis
Attorney, Agent, or Firm—Jack E. Dominik

[57] ABSTRACT

A flexible inert gas impervious housing for the sampler which can be squeezed to an essentially flat configuration in conjunction with a close/open/close valve assembly at both ends of the flexible housing that the buoyancy can be minimized by applying a vacuum to the flexible inert gas impervious housing prior to positioning the same on the sampler array, or prior to securing to a sampler cable for lowering into a body of water is disclosed. Pressure release means are provided to optionally open the valve assemblies when a preselected pressure is reached, usually coordinated with depth of immersion, at which time the sampler flexible housing has the vacuum released and it opens and is flushed by the fluid through which it is passing. Thereafter, means are provided to close the two valve assemblies to entrap the sample, based upon a signal, and to return the sample for discharge from the sampler for further investigation. The method of operation is directed to the sequence of using a sampler in which the valve assemblies are, in coordinated manner, moved to the closed configuration while at the same time storing potential energy in a spring for driving the valve from its closed position to a first open position, and thereafter driving the valve again to a closed position.

2 Claims, 4 Drawing Sheets

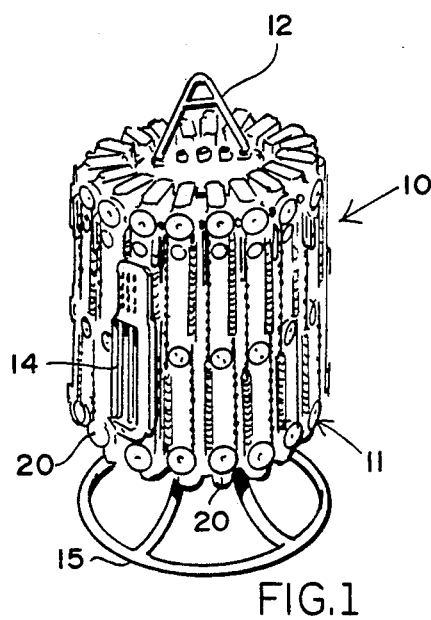
FIG.1
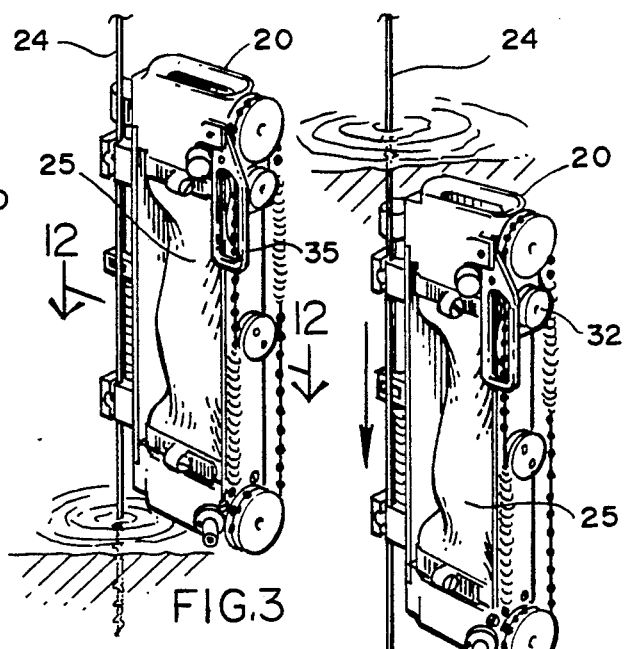
FIG.3  FIG.4
FIG.2
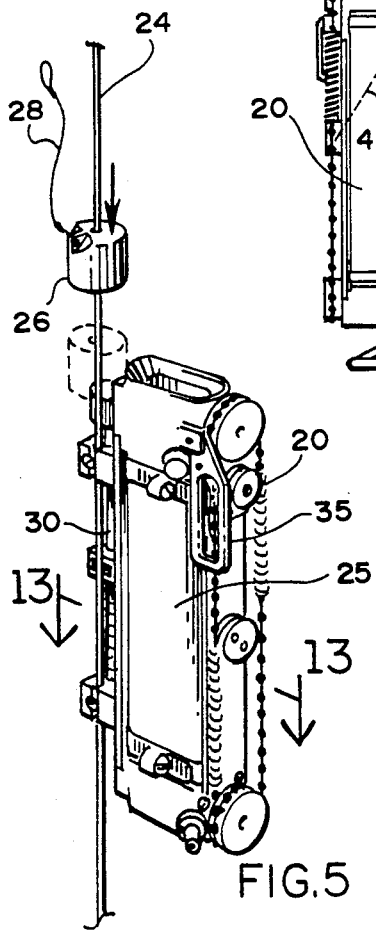
FIG.5
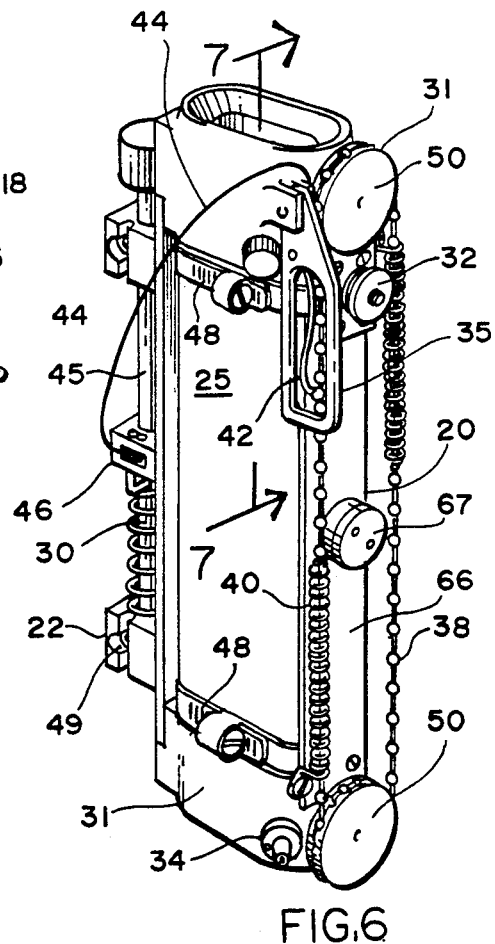
FIG.6

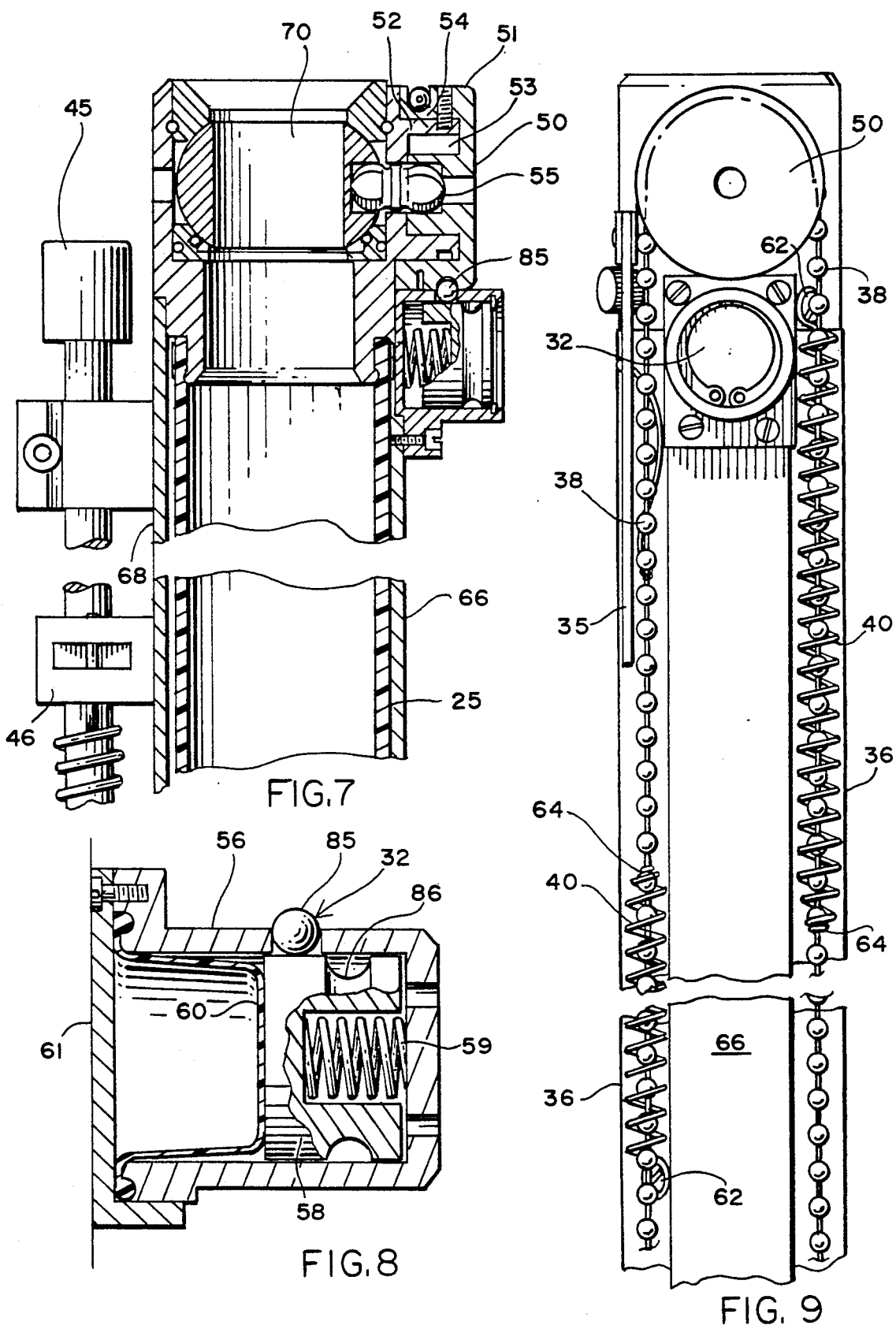

FLUID SAMPLING RESERVOIR AND METHOD

FIELD OF THE INVENTION

The present invention deals with sampling systems of the type found useful in water and other fluid sampling The same can be employed, however, for sampling any type of fluid at varying elevations remote from the people doing the sampling.

SUMMARY OF THE PRIOR ART

The prior art is illustrated by U.S. Pat. No. 4,037,477 now the property of the assignee of this patent application. In the subject patent entitled "Water Sampler Device" additional prior art, seven U.S. patents in number and one British patent have been made a matter of record. The device of U.S. Pat. No. 4,037,477 includes, primarily, an elongated tubular member or bottle 11 having a chamber 12 which is adapted to collect and retain a water sample. Such devices have functioned successfully over the years and are currently in use.

Other examples of the prior art, irrespective of whether shown in issued patents, or known by their tradename are the following. For example, patents owned by the applicants' assignee relating to samplers include U.S. Pat. No. 3242740; 3425664; 3489012; 3815422; 3986635; 4037477; 4091676; 4106751; 4302974; 4347751; 4593570; 4744256 and 4852413. In addition, TRW U.S. Pat. No. 3,866,474; J.D. Richard U.S. Pat. No. 3,367,191; and Scott Gowing Patent assigned to the United States Navy, U.S. Pat. No. 4,635,474 also relate to water samplers. Finally, not in the patent literature, is the product being offered by Falmouth Scientific, Inc. of North Falmouth, Mass. under the trademark "Aqua Pure" sampling system.

One of the principal problems with the prior-art samplers just discussed is that they have a rigid housing or body. When several of these prior-art samplers are secured to a sampling array, and are closed for immersing into a fluid such as an ocean sample to be taken at 5,000 meters, they are lowered usually to a preselected depth beneath any pollution layer, and then opened by a pressure valve, at which time the sampler or bottle itself is filled with water and no longer buoyant. The desired result is to get the sampler array to the bottom as soon as possible. In addition, because the bottles are essentially cylindrical in the prior-art samplers, the upper end portion is a diameter equal to or larger than the bottle itself. This limits, particularly in addition to side mounted release devices and signaling devices, the number of such samplers that can be positioned on a circular sample array. Thus it becomes highly desirable to consider a sampler in which its buoyancy is minimized prior to immersion, and the size of which lends itself to maximizing the number of samplers which can be positioned on a sampling array.

SUMMARY OF THE INVENTION

The present invention stems from the discovery that by utilizing a flexible inert gas impervious housing for the sampler which can be squeezed to an essentially flat configuration in conjunction with a rectangular close/open/close valve assembly at both ends of the flexible housing that the buoyancy can be minimized by applying a vacuum to the flexible inert gas impervious housing prior to positioning the same on the sampler array, or prior to securing to a sampler cable for lowering into a body of water. The subject sampling system normally includes a plurality of samplers such as described in which a drive pulley actuates the two close/open/close valve assemblies coordinated by a combination of a power drive assembly including a driving chain which coacts with a power spring to actuate the valve from its closed to open to closed configuration. Pressure release means are provided to optionally open the valve assemblies when a preselected pressure is reached, usually coordinated with depth of immersion, at which time the sampler flexible housing has the vacuum released and it opens and is flushed by the fluid through which it is passing. Thereafter, means are provided to close the two valve assemblies to entrap the sample, based upon a signal, and to return the sample for discharge from the sampler for further investigation. The method of operation is directed to the sequence of using a sampler in which the valve assemblies are, in coordinated manner, moved to the closed configuration while at the same time storing potential energy in a spring for driving the valve from its closed position to a first open position, and thereafter driving the valve again to a closed position. The sequence involves first cocking the mechanism, and thereafter, while the valve is closed, applying a vacuum which causes the flexible housing to fold in on itself thereby removing a significant portion of the ambient fluid such as air from its interior. Then the sampler is sent to a preselected level at which time pressure sensitive means are directed to open the valves to be flushed by the fluid as the sampler moves. Finally, when the sampler reaches its desired level, the step of signaling the sampler to close both of the valves is activated. Subsequently, the sampler is returned to its original source and emptied of its contents for purposes of further analysis.

In view of the foregoing, it is a principal object of the present invention to provide a sampler which can have its buoyancy reduced to an irreducible minimum.

A further object of the present invention is achieved by utilizing a material for the flexible housing which is essentially inert and gas impervious. This tends to eliminate the problems introduced by a state of the art PVC-type rigid tubular housing in which certain metals in the water can be leached out and the sample effected by any degradation of the housing itself. A related object of the present invention is to utilize the reduced size of the flexible member to compact the sampler itself so that more can be positioned circumferentially about a sampler array.

Yet another object of the present invention is to provide the advantages set forth above in a host environment which is inherently competitive with the prior-art devices which cannot achieve the results achieved by the subject invention.

BRIEF DESCRIPTION OF THE DRAWINGS

Further objects and advantages of the present invention will become apparent as the following description of an illustrative embodiment takes place, as set forth in the accompanying illustrative drawings, in which:

FIG. 1 is a perspective view of an illustrative sampling array of a sampling system having a plurality of samplers secured circumferentially about the sampler array;

FIG. 2 is a front elevation of the sampling system shown in FIG. 1 illustrating the interior sampling array apparatus with a single sampler shown in position secured to the upper adapter plate and the lower adapter plate;

FIG. 3 is a partially diagrammatic view of an illustrative sampler showing the same secured to a sampler cable in position for immersion;

FIG. 4 is a view subsequent to that of FIG. 3 showing the sampler going beneath the surface but still having the housing crushed. It is, however, shown in the process of expanding due to the release of the pressure release and the incipient opening of the close/open/close valve assemblies;

FIG. 5 is a view of the open sampler in the process of being activated by a go devil which, in turn, will trigger a release and permit rotation of the valve to close the sample interiorly of the flexible housing;

FIG. 6 is an enlarged perspective view of the illustrative sampler indicating the basic subassemblies;

FIG. 7 is a longitudinal sectional view of the sampler of FIG. 6 taken essentially along section lines 7—7 of FIG. 6;

FIG. 8 is an enlarged view taken along the section of FIG. 7, but illustrating an alternate diaphragm pressure release element in detail;

FIG. 9 is a side elevation of the view shown in FIG. 6 illustrating the specific details of the power drive assembly;

DESCRIPTION OF A PREFERRED EMBODIMENT

Apparatus

Figure 10:
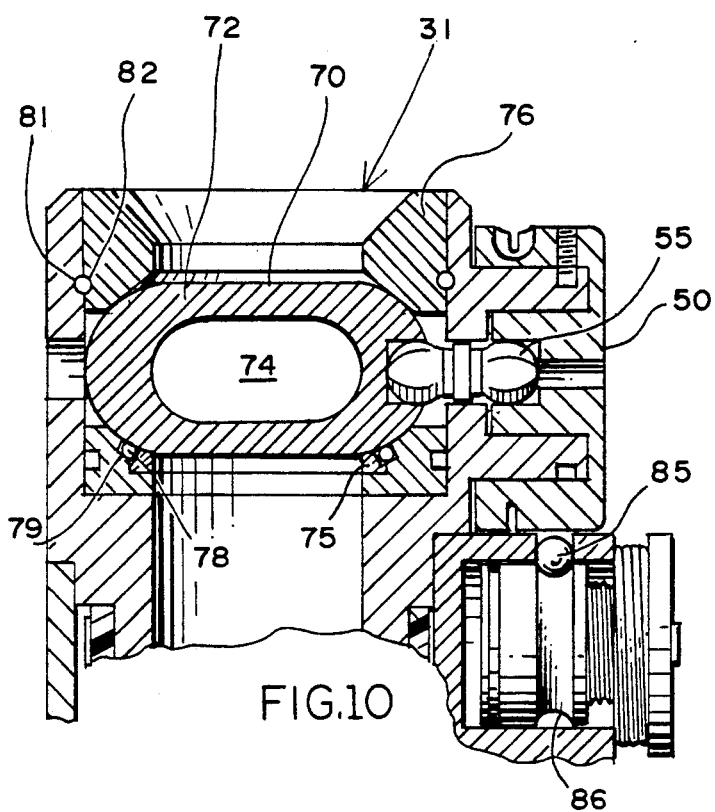
FIG. 10 is an enlarged broken view of the upper close/open/close valve assembly with the valve being shown in the shut off or closed configuration.

The sampling system 10 of the subject invention is shown in its assembled form in FIG. 1 of the accompanying drawings where a reversing thermometer 14 is included in the system. There it will be seen that a sampling array 11 is positioned for securement by means of a hanger 12 at the top and a mount stand 15 at its underneath portion. In FIG. 2 it will be seen that central of the system is the sampling array 11 which includes an upper adapter plate 16 and a lower adapter plate 18. The sampler 20 is secured to the plates 16, 18 by means of upper mount block 21 and lower mount block 22 which are an integral part of the sampler 20. In this embodiment, means are provided in the sampling array 11 to close the samplers 20 at preselected locations or times. Alternatively, individual samplers 20 may be positioned on a sampler cable 24 and activated by go devils 26 to close on the sample at given depths or at a preselected time sequential to each other. Such systems are shown in the applicant's literature 1989 catalogue on page 20. Thus, as shown in FIG. 3 the sampler 20 is ready to go down with the sampler cable 24 to which it is firmly secured. Here it should be noted that the flexible housing 25 is essentially collapsed. It will also be noted that the elongate nature of the valve assembly 31 and particularly as illustrated at the upper portion of FIG. 1, permits a compaction of the number of samplers 20 used on a sampling array 11 when that approach is undertaken. Nonetheless, the same samplers 20 can be utilized on a sampler cable 24 as well.

As shown in FIG. 4, the pressure valve 32 is activating and the flexible housing 25 is beginning to open. Once the same is fully opened and in position to capture a sample, and as illustrated in FIG. 5 a go devil messenger 26 and its associated go devil lanyard 28 descend down the sampler cable 24 to actuate the push rod assembly 30 to close the close/open/close valve assembly 31 which are on both ends of the sampler 20. Alternatively, when the sampler 20 is secured to a sampling array 11 as shown in FIG. 1, the signal instead of being sent by a go devil, is sent by a lanyard release pin on the array as though the array 11 was a plurality of go devils. Once the sample is captured, the sampler cable 24 is raised and the sample is withdrawn through the valve 34 shown at the lower portion of FIG. 6.

A significant advantage is achieved by the present invention because the flexible housing is formed of an essentially inert material. Such materials include floro silicon, or silicon rubber. Exemplary flexible tubes can be acquired commercially from General Electric, Stoffer, and Dow Corning.

Further details of the structure shown in FIG. 6 as to their assembly and relationship each to the other, includes the cocking handle 35. The purpose of the cocking handle 35 is to rotate the power drive assembly 36 to cause the driving chain 38 to activate the power spring 40 to thereby store sufficient potential energy in order to go from the closed to the open to the closed position throughout 180°, at two 90° sequential steps, of the rotation of the valve which is in the upper and lower valve assemblies 31. The spring is locked by the ball pulley release 85 in the groove 86, shown in FIGS. 10 and 11. The power spring 40 encircles the driving chain 38 and is anchored at one end to the driving chain 38. The power spring 40 is secured at its other end secured to the housing of the sampler 20. The cocking handle lanyard 42 is secured to the to driving chain 38. A further release lanyard 44 is also applied to the drive assembly. The push rod 45 is positioned through a center release block 46. A housing clamp 48 is provided at the upper end of the flexible housing 25 and at its lower end and secures the same to the close/open/close valve assembly 31.

To be noted are the drive pulleys 50 at the remote ends of the driving chain 38. As will be described hereinafter, the pulleys 50 activate the two close/open/close valve assemblies 31 in timed and position radial relationship as dictated by the driving chain 38.

In greater detail, it will be seen in FIG. 7, that the pulley 50 has a chain grip 51 and is secured to a pulley bushing 52. A pulley stop 53 is provided interiorly in the form of a pin which rotates in a semi-toroidal-shaped channel in the pulley bushing 52. The axle mount 54 is an integral part of the pulley 50. A valve key 55 in the shape of a modified dog bone secures the pulley 50 to the valve 70 so that the valve 70 is rotated in fixed radial relationship to the pulley 50. A front mount plate 66 and a rear mount plate 68 are utilized to secure the elements together and surround the flexible housing 25 with the front plate serving to mount the pressure release 32 and the rear mount plate 68 serving to mount the push rod assembly 30.

The front plate 66 also mounts an accessory mount 67 which can be used for securing a thermometer, or other accessories to the sampler 20.

As better shown in FIG. 9, the pressure release 32 is positioned on the front mounting plate 66 beneath the upper pulley 50. The power springs 40 are secured to the chain by spring chain anchors 64. There is one on either, side as shown in FIG. 9. The opposite end of the spring 40 is secured to spring housing anchor 62.

Figure 14:
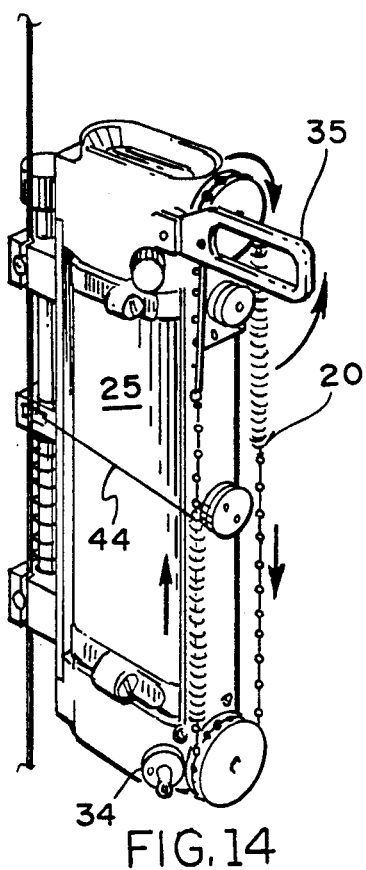
FIG. 14 is a partially diagrammatic schematic view showing the cocking of the sampler and preparing the same for mounting in the sampler system on the sampling array.

Turning now to FIG. 8, it will be seen that the pressure release 32 is contained in a pressure release housing 56 in which a piston 58 is urged by means of compression spring 59 to close the diaphragm 60. In FIG. 7 an alternative embodiment is shown which omits a diaphragm. The housing 56 and its contained elements are secured to a pressure release mounting plate 61. Provision is made, as shown in both FIGS. 7 and 8, for a ball pulley release 85 which goes in and out of a ball receiving release groove 86. The ball 85 rests atop an orifice in the housing 56 until the piston 58 moves far enough against the diaphragm 60 to align the ball receives groove 86 underneath the ball 85 whereupon the ball drops activating the power spring to rotate the pulley, and accomplishes the first 90° of opening of the valve 70. At this point, with reference to FIG. 14, it will be seen that the lanyard 44 which was loose at the time the sampler was activated for descending is pulled taught, by the power spring so that the valve is in the open position, but with the power spring maintaining sufficient potential energy to subsequently close the valve when the lanyard 44 is released.

Figure 11:
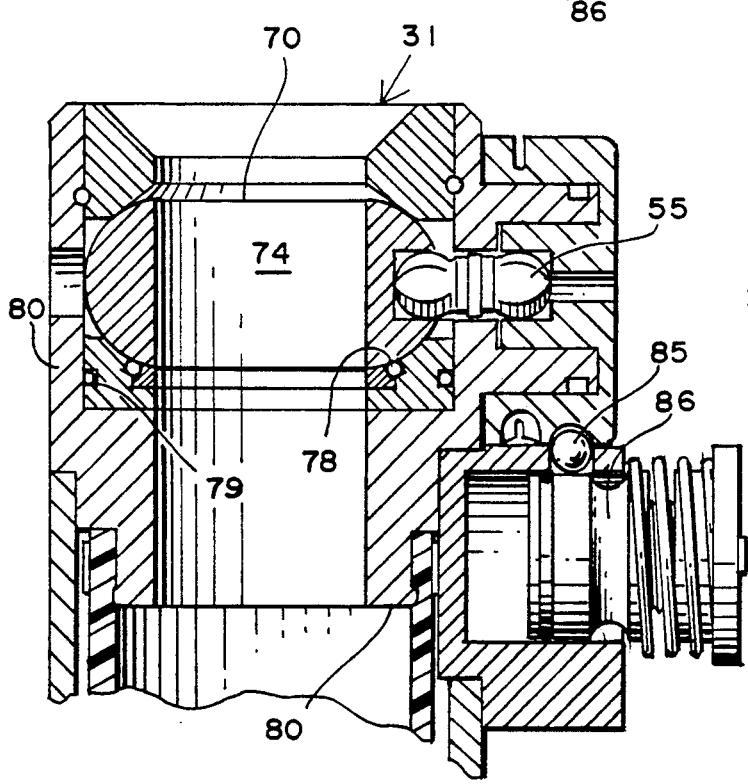
FIG. 11 is a view sequential to that of FIG. 10 showing the valve in the open position.

Specifics of the valve assembly of the close/open/close valve 31 appear on sequential FIGS. 10, 11, 12, and 13. Turning now to FIG. 10, it will be seen that the close/open/close valve assembly 31 has as its key element a valve 70 secured by means of the valve key 55 to a drive pulley 50. In this connection it should be understood that the valve assembly 31 at the upper portion of the sampler is a mirror image of the valve assembly 31 provided at the bottom. The only difference between the upper and lower portions of the entire sampler are the provision of the pressure release 32 at the upper portion, and the push rod assembly at the side opposite the pressure release. The valve 70 has a body portion 72 and a central port 74. The valve 70 is seated in a lower seal 75 and sandwiched in place between the lower seal 75 and the upper nose cone 76. Optionally, an O-ring 78 is provided in an O-ring seat in the lower seal 75. It will be appreciated that if the lower seal is formed out of a sealing-type material, the O-ring may be unnecessary. What is necessary, however, is to seal the valve 70 in the closed position so that fluid cannot pass through the valve port 74. FIG. 11 is sequential to FIG. 10 and shows the valve port 74 and the valve 70 in the open position ready to permit fluid to flush through into the flexible housing 25. To be noted is the different location of the pressure valve 32 and the ball pulley release 85 with regard to its release groove 86 when contrasting FIGS. 10 and 11.

Figure 12:
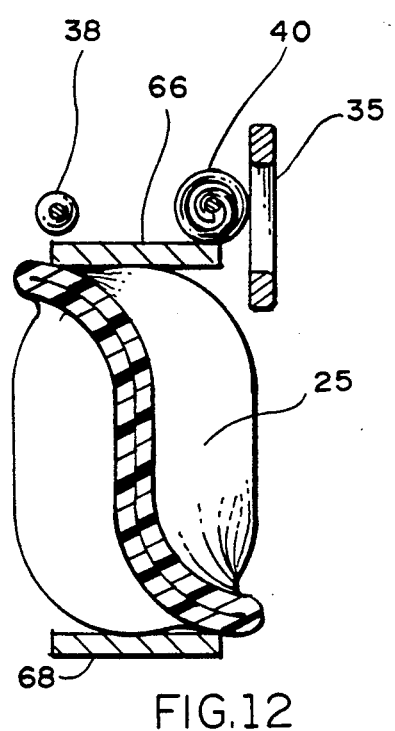
FIG. 12 is a transverse sectional View taken along section line 12—12 of FIG. 3 and showing the flexible housing in the collapsed configuration.
Figure 13:
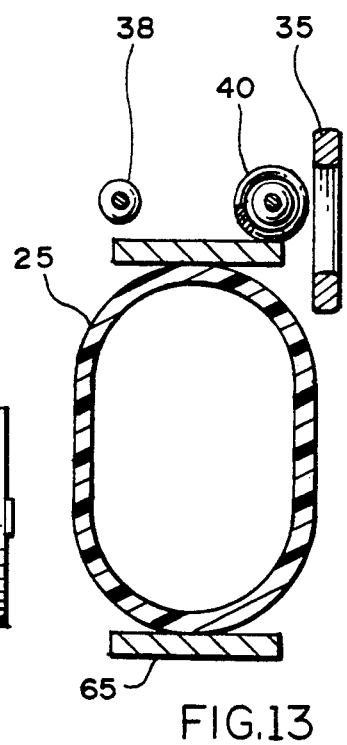
FIG. 13 is taken along section line 13—13 of FIG. 5 showing the flexible housing in its enlarged configuration when the valves are open.

As will be seen diagrammatically in FIG. 12, the flexible housing 25 is collapsed diagonally across the front mounting plate 66 and the rear mounting plate 68. Also to be noted is the orientation of the drive chain 38 on both sides of the front mounting plate 66. In addition, the cocking handle 35 is shown in relationship to the power spring 40. As shown in FIG. 6, the cocking 35 activates cocking handle lanyard 42 to move the driving chain 38. In FIG. 13 which is sequential to that of FIG. 12, all of the elements just described are shown in their same relationship with the exception of the flexible housing 25 being in its open or expanded configuration. The go devil messenger 26 releases the lanyard 44 which permits closure of the ends.

Method

Figure 15:
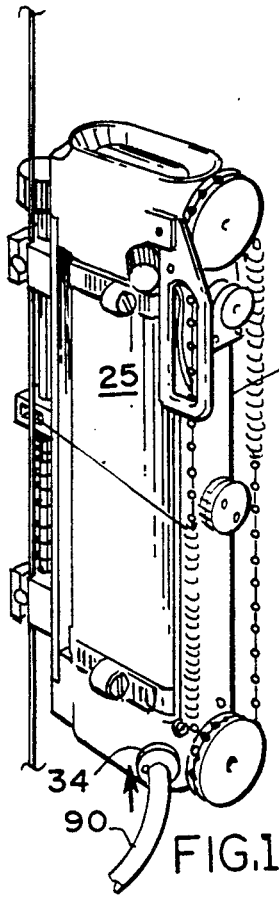
FIG. 15 is a view sequential to FIG. 14 illustrating how a vacuum is applied to the sampler and crushes the flexible housing.
Figure 16:
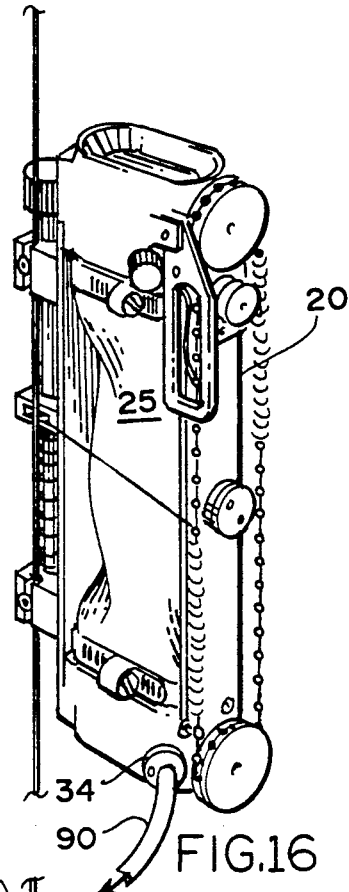
FIG. 16 shows the housing collapsed and ready to remove the vacuum line.

The method of the present invention will be best understood as the following description traces the steps of operation as illustrated diagrammatically in FIGS. 14-19. There it will be seen in FIG. 14 that the cocking action is undertaken by activating the cocking handle 35 which rotates the power drive 36 to sufficiently store potential energy in the power spring 40 for first opening 90 and thereafter closing 90° in the same direction of rotation as the opening. Also shown diagrammatically are the upper mount block 21 and lower mount block 22 which can be secured to the upper adapter plate 16 and lower adapter plate 18 of the sample array 11. Thereafter as shown in FIG. 15, the valve 34 is secured to a vacuum line 90 and a vacuum applied. The valve 34 permits withdrawing of the contents of the flexible housing 25 until it is essentially collapsed as shown in FIG. 16. At that point the valve 34 is closed and the vacuum line 90 is removed.

Figure 17:
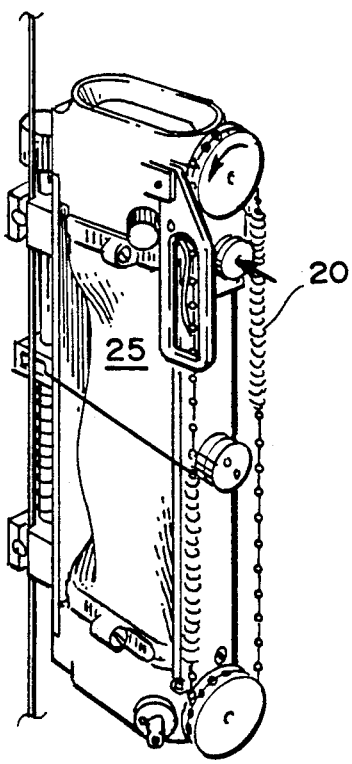
FIG. 17 is a sequential view to that of FIG. 16, but illustrating how the collapsed sampler is descending shortly before the pressure release activates the valves to the open configuration.
Figure 18:
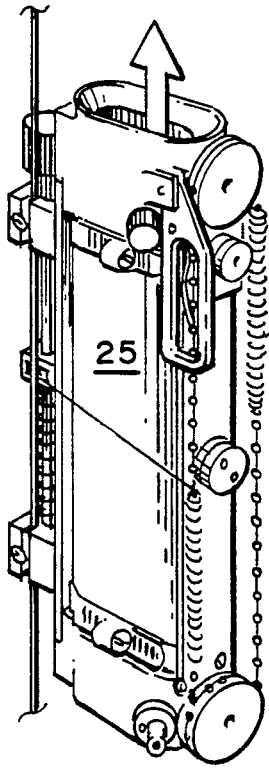
FIG. 18 is a view sequential to FIG. 17 showing the sampler open and being flushed as it descends to its predetermined depth for being closed.

Sequentially, as shown in FIG. 17, the sampler 20 with its collapsed flexible housing 25 proceeds downwardly in a fluid. Upon the activation of the pressure release 32, the valve assemblies 31 are open, and the fluid passes through the flexible housing 25 as illustrated by the arrows in FIG. 18. Finally, when it is desired to close the valve 70 a go devil 26 or other signal is sent to the push rod assembly 30, and the final 90° of rotation of the valve 70 takes place turning it into the closed configuration as illustrated in FIG. 10. The open configuration as illustrated in FIG. 11, is that which is shown particularly in FIG. 18.

Figure 19:
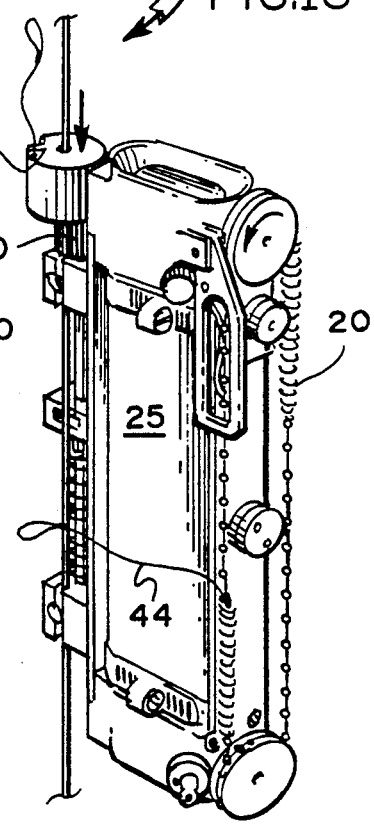
FIG. 19 illustrates diagrammatically the activation to close the sample by sending a go devil down the sampler cable to engage a tripping assembly for accomplishing the final closure.

The method of the invention contemplates the steps as just shown and described in which there is a first cocking action to close the valve and to mount the same either on a sampling array 11 or a sampler cable 24. Prior to this action, but after the cocking, a vacuum is applied to the flexible chamber 25 through the valve 34 and the vacuum line 90 essentially as shown and described in FIGS. 15 and 16, with the vacuum line being removed and the valve closed after the flexible housing 25 has collapsed. The sampler is then ready for the step of immersing the same into a fluid and upon a preselected depth or pressure being reached, the first tripping action engages through the power spring 40 and rotates both of the drive pulleys 50 until the valve 70 is in the open configuration to permit water to flush through the entire sampler 20 in the position as shown in FIG. 11. Thereafter, when the correct depth is reached for encapsulating the sample, the action as shown in FIG. 19 of tripping the push rod assembly 30 and releasing the final release of the lanyard 44 takes place and the sampler is brought to its point of origination. Once at the point of origination, the sampler 20 can be engaged by a closed circuit withdrawal through the valve 34. The advantage of this closed circuit discharge permits to retain any dissolved gases which may be in the fluid which is being withdrawn. It, furthermore, prevents ambient air from contaminating the sample which may otherwise be withdrawn into either an inert gas filled container or even a collapsible container which is filled by the contained fluid as it passes out.

It will be understood that various changes in the details, materials and arrangements of parts which have been herein described and illustrated in order to explain the nature of the invention, may b-e made by those skilled in the art within the principle and scope of the invention as expressed in the appended claims.

What is claimed is:

1. A sampling system comprising, in combination,
   a sampling array, said array including a hanger and a mount stand and upper adapter plates and lower adapter plates,
   a plurality of samplers for mounting to said sampler array,
   each of said samplers having a close/open/close valve assembly at two opposed ends,
   a flexible housing secured to each of the close/open/close valve assemblies,
   means for drawing a vacuum on the inner portion of the flexible housing to collapse the same,
   and means for sequentially driving the valve assemblies from a closed position to an open position, and thereafter from the open position to a final closed position.
2. In the sampling system of claim 1,
   said valve having a body portion,
   said body portion having an elongate port at its interior portion,
   said valve being actuated by a drive pulley,
   said drive pulley being actuated by a power drive which coordinates the activation of the opposed close/open/close valve assemblies.

* * * * *